US011013465B2

(12) United States Patent
Yang et al.

(10) Patent No.: US 11,013,465 B2
(45) Date of Patent: May 25, 2021

(54) BIOLOGICAL FEATURE DETECTION APPARATUS AND ELECTRONIC TERMINAL

(71) Applicant: SHENZHEN GOODIX TECHNOLOGY CO., LTD., Shenzhen (CN)

(72) Inventors: Wangwang Yang, Shenzhen (CN); Zhiyao Liu, Shenzhen (CN); Chang Liu, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 141 days.

(21) Appl. No.: 16/141,925

(22) Filed: Sep. 25, 2018

(65) Prior Publication Data

US 2019/0021670 A1   Jan. 24, 2019

Related U.S. Application Data

(63) Continuation of application No. PCT/CN2017/091030, filed on Jun. 30, 2017.

(51) Int. Cl.
*A61B 5/00* (2006.01)
*A61B 5/024* (2006.01)
*H04R 1/10* (2006.01)
(Continued)

(52) U.S. Cl.
CPC ........ *A61B 5/6816* (2013.01); *A61B 5/02427* (2013.01); *A61B 5/02438* (2013.01);
(Continued)

(58) Field of Classification Search
CPC . A61B 5/6816; A61B 5/6817; A61B 5/02438; A61B 5/02427; A61B 5/14552;
(Continued)

(56) References Cited

U.S. PATENT DOCUMENTS

| 2010/0217098 | A1 | 8/2010 | LeBoeuf et al. |
| 2012/0197093 | A1 | 8/2012 | LeBoeuf et al. |
| 2012/0253159 | A1* | 10/2012 | Medina ............... A61B 5/14552 600/340 |
| 2013/0131519 | A1* | 5/2013 | LeBoeuf .............. A61B 5/0077 600/476 |

(Continued)

FOREIGN PATENT DOCUMENTS

| CN | 103549962 A | 2/2014 |
| CN | 204392514 U | 6/2015 |

(Continued)

*Primary Examiner* — Eric F Winakur
*Assistant Examiner* — Abid A Mustansir
(74) *Attorney, Agent, or Firm* — Brion Raffoul (57) ABSTRACT

A biological feature detection apparatus and an electronic device are provided. The apparatus includes a light emitting unit and a light receiving unit. The light emitting unit is configured to emit light to a detection surface of a biological tissue, the light emitted by the light emitting unit is processed by the biological tissue and then transmitted to the light receiving unit, and the light receiving unit is configured to receive the light and perform a photoelectric conversion to generate an original electrical signal for biological feature detection; the light emitting unit and the light receiving unit are attached to the detection surface of the biological tissue. As such, the signal-to-noise ratio of the original electrical signal is improved and accuracy of biological feature detection is enhanced.

14 Claims, 9 Drawing Sheets

(51) Int. Cl.
*A61B 5/0205* (2006.01)
*G06K 9/00* (2006.01)
*A61B 5/1455* (2006.01)

(52) U.S. Cl.
CPC ......... *A61B 5/6817* (2013.01); *H04R 1/1016* (2013.01); *A61B 5/0205* (2013.01); *A61B 5/14552* (2013.01); *G06K 9/00885* (2013.01); *G06K 2009/00932* (2013.01); *G06K 2009/00939* (2013.01); *H04R 1/1041* (2013.01)

(58) Field of Classification Search
CPC .. A61B 5/0205; H04R 1/1016; H04R 1/1041; G06K 2009/00932; G06K 9/00885; G06K 2009/00939
See application file for complete search history.

(56) References Cited

U.S. PATENT DOCUMENTS

| | | | |
|---|---|---|---|
| 2013/0303864 A1* | 11/2013 | Chen | A61B 5/14552 600/306 |
| 2015/0208933 A1* | 7/2015 | Satomi | A61B 5/02416 600/479 |
| 2017/0118551 A1 | 4/2017 | Wagner et al. | |

FOREIGN PATENT DOCUMENTS

| | | |
|---|---|---|
| CN | 205697764 U | 11/2016 |
| CN | 205921723 U | 2/2017 |
| WO | 2016119665 A1 | 8/2016 |

* cited by examiner

BIOLOGICAL FEATURE DETECTION APPARATUS AND ELECTRONIC TERMINAL

CROSS-REFERENCE TO RELATED APPLICATIONS

The present disclosure is a continuation of international application No. PCT/CN2017/091030, filed on Jun. 30, 2017, which is hereby incorporated by reference in its entireties.

TECHNICAL FIELD

Embodiments of the present application relate to the technical field of biological feature detection, and in particular, relate to a biological feature detection apparatus and an electronic terminal.

BACKGROUND

Rapid development of smart devices, for example, emergence of smart earphones, facilitates practice of applications having a healthcare function, for example, detection of heart rate, blood oxygen and the like biological features. Specifically, these smart devices are used in scenarios of monitoring the heart rate and blood oxygen during exercise or movement to judge whether the biological feature of a user is normal, or monitoring the heart rate and blood oxygen during sleeping to judge whether the biological feature of a user is normal.

With regard to the practice of the above applications having the healthcare function, the current commonly used manner is: measuring the biological feature based on the optical theory, for example, the light reflection theory and the light transmission theory. Using the light reflection theory as an example, the light emitted by a light emitter is incident to the biological tissue and then reflected by the biological tissue, and a light receiver receives the reflected light and performs biological feature detection based on the reflected light. During this process, the incident light is reflected under effects (absorption and diffusion) of the blood in the tissue and then the reflected light is formed. Since the blood in the tissue may be periodically changed, the biological feature may be obtained by sensing and analyzing the reflected light. Analogously, with respect to the light transmission theory, the biological feature may be obtained by sensing and analyzing the transmitted light.

SUMMARY

The inventors have found out over years of study that the biological feature of an ear detected based on light reflection theory has a low accuracy, since a biological feature detection signal generated based on an emitted light has a small signal-to-noise ratio.

Embodiments of the present application are intended to provide a biological feature detection apparatus and an electronic terminal, to at least solve the above technical problem in the prior art.

To achieve the objective of the present application, embodiments of the present application provide a biological feature detection apparatus. The apparatus includes: a light emitting unit and a light receiving unit; wherein the light emitting unit is configured to emit light to a detection surface of a biological tissue, the light emitted by the light emitting unit being processed by the biological tissue and then transmitted to the light receiving unit, and the light receiving unit is configured to receive the light and perform a photoelectric conversion to generate an original electrical signal for biological feature detection; the light emitting unit and the light receiving unit are configured to fitted the detection surface of the biological tissue to improve a signal-to-noise ratio of the original electrical signal; the biological tissue is an ear, and during biological feature detection, at least one of the light receiving unit and the light emitting unit is fitted to a tragus inner-side region; or at least one of the light receiving unit and the light emitting unit is fitted to a region between an inferior crus of antihelix and a crus of helix; or at least one of the light receiving unit and the light emitting unit is fitted to a region between an antihelix and a crus of helix; or at least one of the light receiving unit and the light emitting unit is fitted to a cimba concha region; or at least one of the light receiving unit and the light emitting unit is fitted to an earlobe region; or at least one of the light receiving unit and the light emitting unit is located in a concha cavity; or at least one of the light receiving unit and the light emitting unit is located in a region enclosed by the crus of helix, an ear canal entrance and the antihelix close to an antitragus.

Optionally, in any embodiment of the present application, if the light receiving unit is fitted to the tragus inner-side region, the light emitting unit is located in an underneath connection region between an intertragic notch and an outer ear canal entrance; or if the light emitting unit is fitted to the tragus inner-side region, the light receiving unit is located in an underneath connection region between an intertragic notch and an outer ear canal entrance.

Optionally, in any embodiment of the present application, the apparatus further includes: a wearing assistance mechanism; wherein the light receiving unit and the light emitting unit are arranged on the wearing assistance mechanism, such that at least one of the light receiving unit and the light emitting unit is fitted to the region between the inferior crus of antihelix and the crus of helix or such that at least one of the light receiving unit and the light emitting unit is fitted to the region between the antihelix and the crus of helix.

Optionally, in any embodiment of the present application, the apparatus further includes: a first substrate and a second substrate; wherein the light emitting unit is arranged on the first substrate, and the light receiving unit is arranged on the second substrate.

Optionally, in any embodiment of the present application, the first substrate and/or the second substrate is a rigid substrate; or the first substrate and/or the second substrate is a flexible substrate.

Optionally, in any embodiment of the present application, the apparatus further includes: an optical shielding unit, configured to shield or absorb the light emitted by the light emitting unit to prevent the light emitted by the light emitting light from being directly transmitted to the light receiving unit without being processed by the biological tissue; and/or further comprising: a light guiding unit, configured to guide the light emitted by the light emitting unit to the detection surface of the biological tissue, and/or configured to guide the light being processed by the biological tissue to the light receiving unit.

Optionally, in any embodiment of the present application, the optical shielding unit and the light guiding unit are integrally arranged, or the optical shielding unit and the light guiding unit are separately arranged.

Optionally, in any embodiment of the present application, a surface shape of the light guiding unit and/or the optical shielding unit mates with the detection surface of the biological tissue.

Optionally, in any embodiment of the present application, the apparatus further includes: a processing circuit, wherein the processing circuit is configured to perform an analog-to-digital conversion for the original electrical signal to form a digital signal and filters the digital signal; and/or further comprising: a control circuit, wherein the control circuit is configured to control the light emitting unit to emit light to the biological tissue and control the light receiving unit to receive the light.

Optionally, in any embodiment of the present application, the apparatus further includes: a processor; wherein the processor is configured to perform biological feature detection according to the original electrical signal.

Optionally, in any embodiment of the present application, the light emitting unit and the light receiving unit are connected via a flexible member, and a relative position and/or a relative angle between the light emitting unit and the light receiving unit is adjusted via the flexible member.

Optionally, in any embodiment of the present application, the relative position is a linear distance between a geometric center of the light emitting unit and a geometric center of the light receiving unit, and the relative angle is a normal angle between an outer surface of the light emitting unit and an outer surface of the light receiving unit.

Optionally, in any embodiment of the present application, a normal of the light receiving unit facing towards an outer surface of the detection surface is parallel to a normal of a detection surface of the light receiving unit; or a normal of the light emitting unit facing towards an outer surface of the detection surface is parallel to a normal of the detection surface.

Optionally, in any embodiment of the present application, the biological feature is a heart rate feature and a blood oxygen feature based on a photoplethysmogram signal.

Optionally, in any embodiment of the present application, the apparatus further includes: an elastic unit; wherein, during biological feature detection, the elastic unit is configured to enable the light emitting and/or the light receiving unit to be closely fitted to the detection surface of the biological tissue.

Embodiments of the present application further provide an electronic terminal. The electronic terminal includes the above described biological feature detection apparatus.

In the biological feature detection apparatus according to the embodiments of the present application, the light emitting unit is configured to emit light to a detection surface of a biological tissue, the light emitted by the light emitting unit is processed by the biological tissue and then transmitted to the light receiving unit, and the light receiving unit is configured to receive the light and perform a photoelectric conversion to generate an original electrical signal for biological feature detection; the light emitting unit and the light receiving unit are configured to fit the detection surface of the biological tissue. As such, signal-to-noise ratio of the original electrical signal is improved and accuracy of biological feature detection is enhanced.

DETAILED DESCRIPTION

Practice of the present application is described in detail with reference to drawings and specific embodiments, such that the practice of addressing the technical problem using the technical means according to the present application and achieving the technical effects may be better understood and conducted.

In the biological feature detection apparatus according to the embodiments hereinafter of the present application, the light emitting unit is configured to emit light to a detection surface of a biological tissue, the light emitted by the light emitting unit is processed by the biological tissue and then transmitted to the light receiving unit, and the light receiving unit is configured to receive the light and perform a photoelectric conversion to generate an original electrical signal for biological feature detection; the light emitting unit and the light receiving unit are configured to fit the detection surface of the biological tissue to improve a signal-to-noise ratio of the original electrical signal.

In the embodiments hereinafter, the detection surface is determined based on the arterial branch density, the vein branch density, and flatness of different positions of the ear. It should be noted that under inspiration of the embodiments hereinafter, without paying any creative effort, persons skilled in the art would envisage that the detection surface may be determined based on one or a combination of the arterial branch density, the vein branch density, and flatness of different positions of the ear in some specific application scenarios.

In the embodiments hereinafter, the biological feature is a heart rate feature or a blood oxygen feature or the like biological feature detected based on the light theory, for example, the heart rate feature and the blood oxygen feature based on a photoplethysmogram signal.

Figure 1:
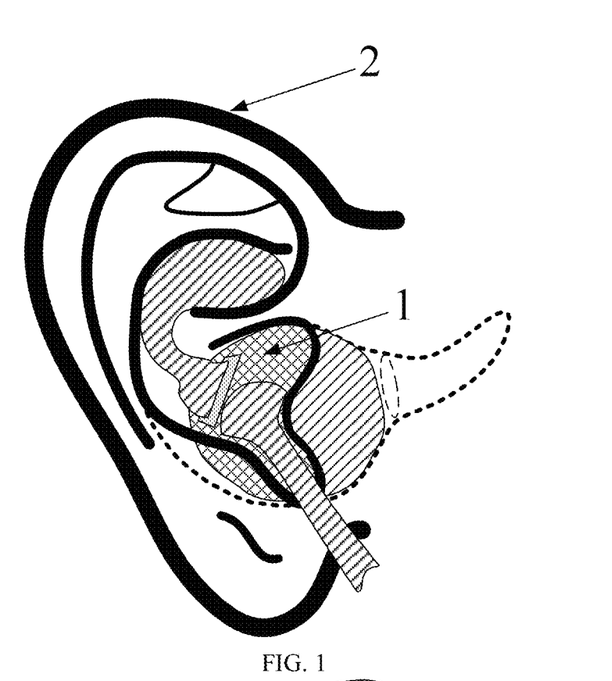
FIG. 1 is a schematic structural diagram of a biological feature detection apparatus according to the first embodiment of the present application.

FIG. 1 is a schematic structural diagram of a biological feature detection apparatus according to the first embodiment of the present application. In this embodiment, a biological feature detection apparatus 1 is practiced in the form of an earphone, which may also be understood as integrating the biological feature detection apparatus on an earphone structure. For clear description of application of the biological feature detection apparatus, FIG. 1 also illustratively shows an ear 2 as an example of the biological tissue. If the biological feature detection is practiced by using the earphone structure, a position relationship between the light emitting unit and the light receiving unit, and the detection surface on the ear is as described in the embodiments hereinafter. When the detection surface is at the following positions, few modifications are made to the structure of the traditional earphone, and the earphone may be comfortably worn.

Figure 2:
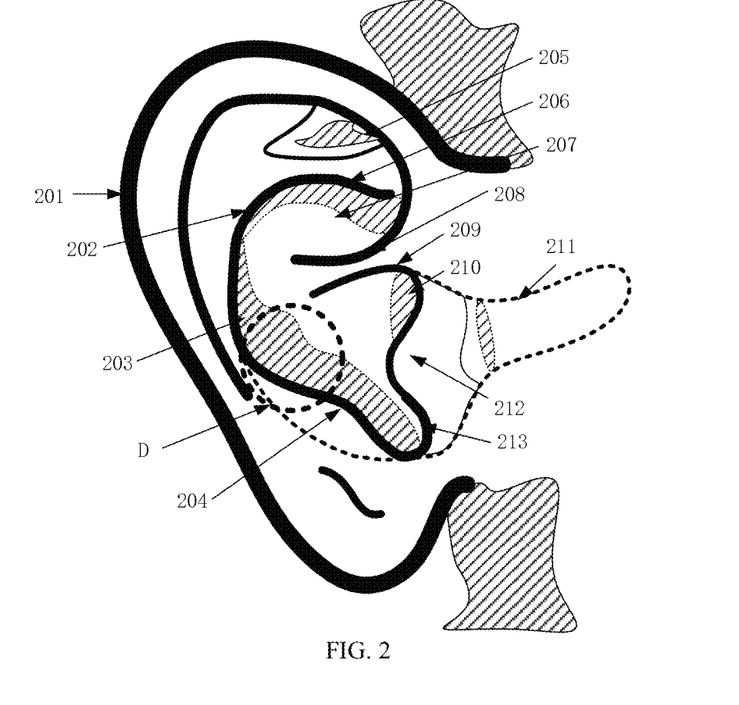
FIG. 2 is a schematic diagram of candidate regions of a detection surface of an ear according to the second embodiment of the present application.

FIG. 2 is a schematic diagram of candidate regions of a detection surface of an ear according to the second embodiment of the present application. As illustrated in FIG. 2, corresponding to FIG. 1, a portion of the features of the ear 2 include: a helix 201, an antihelix 202, an auricular concha 203, an antitragus 204, a triangular fossa 205, an inferior crus of antihelix 206, a cimba concha 207, a crus of helix 208, a supratragic notch 209, an outer ear canal entrance 210, an ear canal 211, a tragus 212, and an intertragic notch 213.

In the embodiments hereinafter, description is given by using the scenario where the biological feature detection apparatus is practiced with the earphone as a specific product. To better determine the detection surface in a feature region of the ear as illustrated in FIG. 2, after the arterial branches, the vein branches and flatness of different feature regions of the ear are comprehensively analyzed, a relatively flat feature region where the arterial branch density and the vein branch density are great is used as the detection surface.

Accordingly, in the embodiments hereinafter, exemplarily, the light emitting unit and/or the light receiving unit are arranged in an inner side region of the tragus 211, or in an underneath connection between the intertragic notch 212 and the outer ear canal entrance 210, a concha cavity region of the auricular concha 203, a region extending to the supratragic notch 209, a region between the inferior crus of antihelix 206 (or the antihelix 202) and the crus of helix 208, a region of the auricular concha 203, a region of the cimba concha 207, a region of the earlobe (not illustrated in the drawings); or the light emitting unit and/or the light receiving unit is arranged in a region enclosed by the crus of helix, the ear canal entrance and the antihelix close to the antitragus. For different users, these regions are morphologically stable. That is, the biological feature detection apparatus has good compatibility with regard to the ears of different users, such that a detection signal having a high signal-to-noise ratio may be simply generated, and accuracy of biological feature detection is ensured.

In a specific embodiment, the light emitting unit and/or the light receiving unit are arranged in a region D enclosed by the crus of helix, the ear canal entrance and the antihelix close to the antitragus; the light emitting unit and the light receiving unit in the biological feature detection apparatus is closely fitted to the detection surface. Since the arterial branches and the vein branches are densely distributed at this position, the obtained original electrical signal has a great signal-to-noise ratio. Therefore, the original electrical signal has a strong anti-interference capability, and thus accuracy of biological feature detection is further ensured. In addition, since different ear shapes are slightly different in the region D, if the biological feature detection apparatus is integrated on an earphone, the earphone is well compatible with the ears. Therefore, the earphone has a wide application range, and thus achieves a high accuracy of signal detection for different users.

Figure 3A:
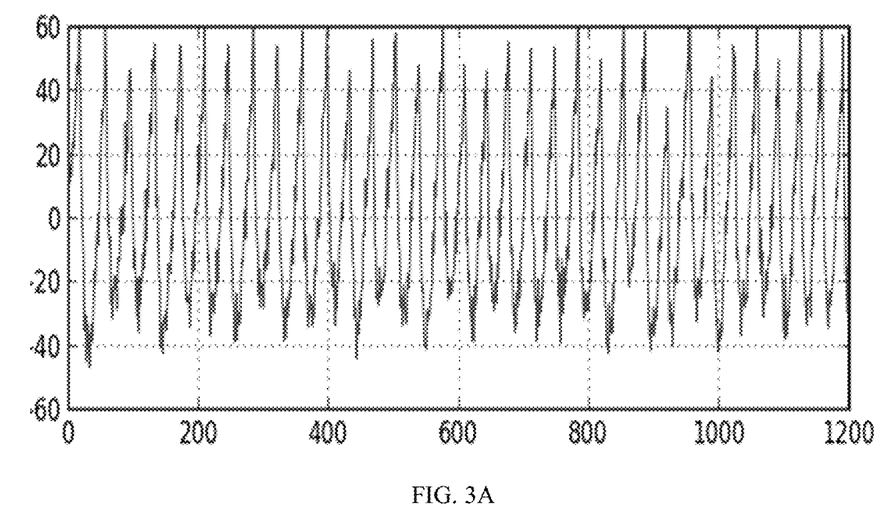
FIG. 3A and FIG. 3B are schematic diagrams before and after a sample detection signal is filtered in a tragus inner-side region according to the third embodiment of the present application.
Figure 3B:
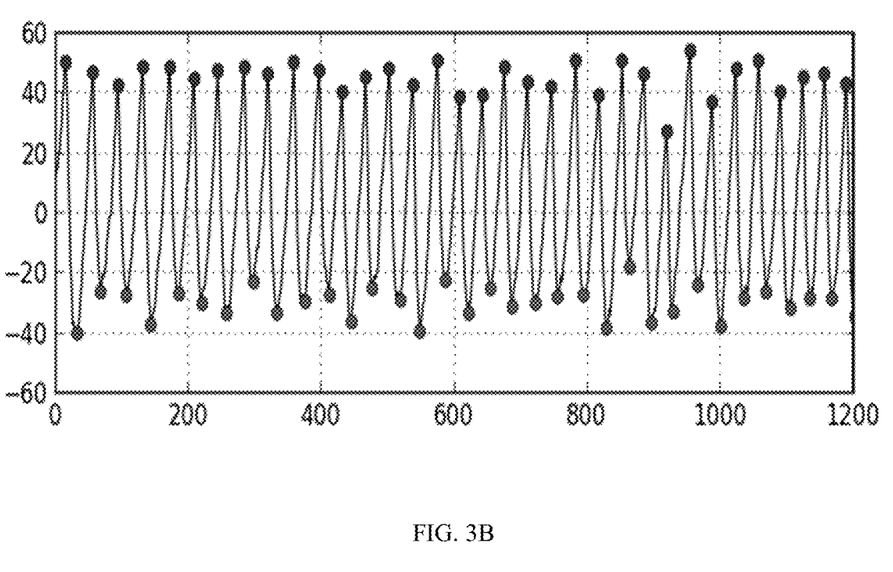

FIG. 3A and FIG. 3B are schematic diagrams before and after a sample original electrical signal in a tragus inner-side region according to the third embodiment of the present application. As illustrated in FIG. 3A and FIG. 3B, variations of the original electrical signal are relatively stable, and quality of the electrical signal is high. Accordingly, the arterial branches, the vein branches and the flatness in the inner-side region of the tragus 212 are conditions for determining the detection surface.

Figure 4:
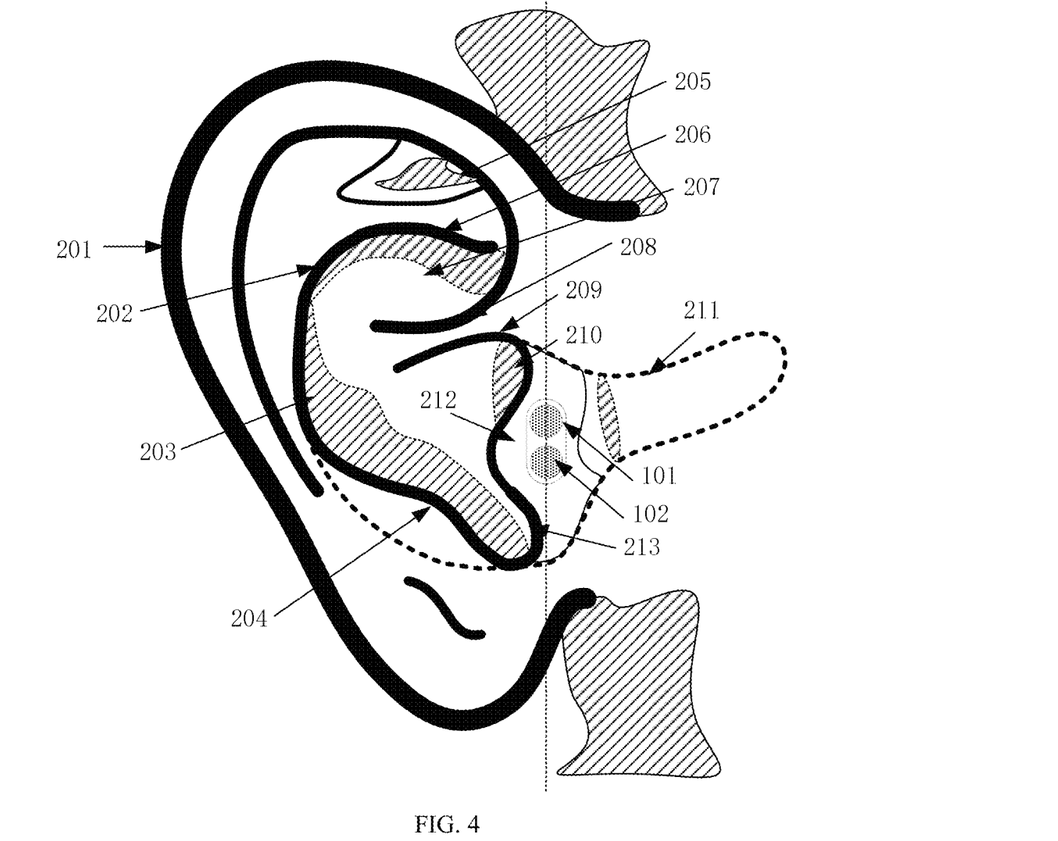
FIG. 4 is a schematic diagram of wearing an earphone on the ear according to the fourth embodiment of the present application.

FIG. 4 is a schematic diagram of wearing an earphone on the ear according to the fourth embodiment of the present application. As illustrated in FIG. 4, in this embodiment, during biological feature detection, the light receiving unit 102 and the light emitting unit 101 are fitted to an inner-side region of the tragus 212. Specifically, a reference line R may be defined, and when attaching the light receiving unit 102 and the light emitting unit 101 to the inner-side region of the tragus 212, geometric centers of the light receiving unit 102 and the light emitting unit 101 are located on the reference line R. Since the arterial branches and the vein branches are densely distributed in the inner-side region of the tragus 212 and the flatness is good, the light receiving unit 102 and the light emitting unit 101 may be seamlessly fitted to the inner-side region of the tragus 212.

In this embodiment, to enable the light receiving unit 102 and the light emitting unit 101 to fit to the inner-side region of the tragus 212, the light receiving unit 102 and the light emitting unit 101 may be integrated at a shell fitted to the inner-side region of the tragus 212 after the earphone is worn, with no need to arrange an assistance mechanism, such that the biological feature detection apparatus including the light receiving unit 102 and the light emitting unit 101 are integrally closely fitted to the inner-side region of the tragus.

Figure 5:
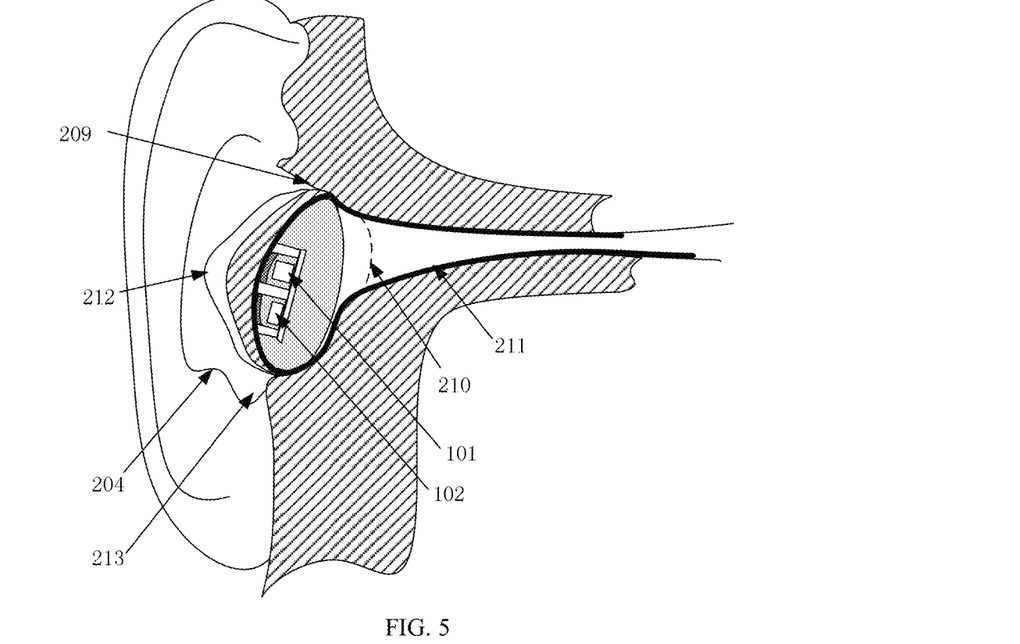
FIG. 5 is a schematic diagram of wearing an earphone on the ear according to the fifth embodiment of the present application.

FIG. 5 is a schematic diagram of wearing an earphone on the ear according to the fifth embodiment of the present application. As illustrated in FIG. 5, in this embodiment, like the sixth embodiment illustrated in FIG. 4, although during biological feature detection, the light receiving unit 102 and the light emitting unit 101 are fitted to the inner-side region of the tragus, the specific position to which the receiving unit 102 and the light emitting unit 101 are fitted in the inner-side region of the tragus 212 is distal from the outer ear canal entrance. Since the arterial branches and the vein branches are densely distributed in the inner-side region of the tragus 212, and the flatness is good, the light receiving unit 102 and the light emitting unit 101 may be seamlessly fitted to the inner-side region of the tragus 212.

In this embodiment, similar to the embodiment illustrated in FIG. 4, to enable the light receiving unit 102 and the light emitting unit 101 to be fitted to the inner-side region of the tragus 212, the light receiving unit 102 and the light emitting unit 101 may be integrated at a shell fitted to the inner-side region of the tragus 212 after the earphone is worn, with no need to arrange an assistance mechanism, such that the biological feature detection apparatus including the light receiving unit 102 and the light emitting unit 101 are integrally closely fitted to the inner-side region of the tragus.

Figure 6:
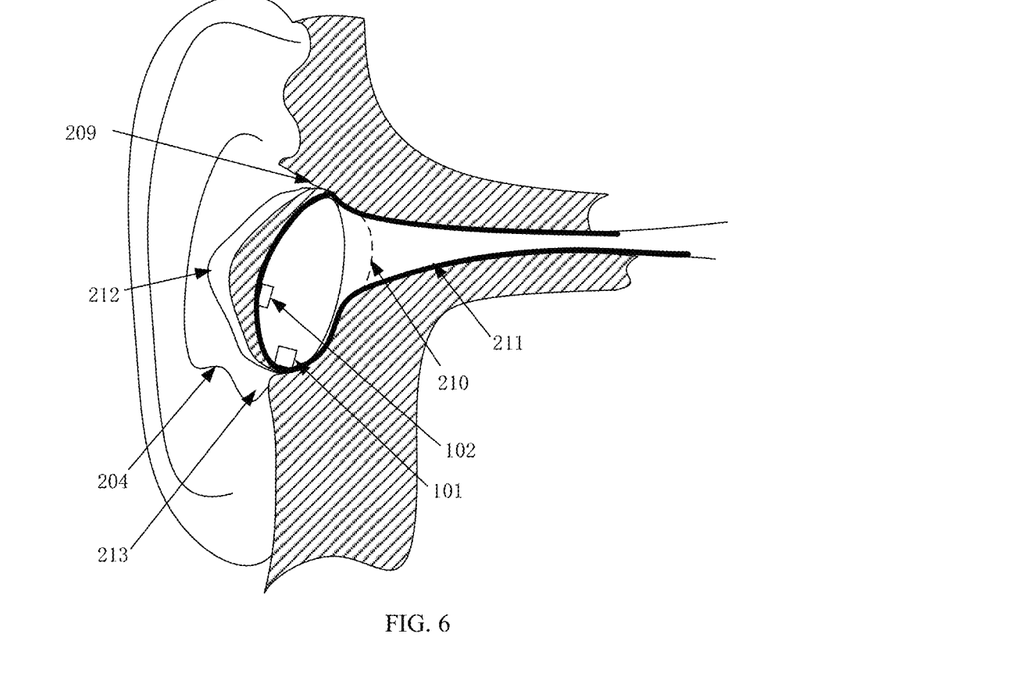
FIG. 6 is a schematic diagram of wearing an earphone on the ear according to the sixth embodiment of the present application.

FIG. 6 is a schematic diagram of wearing an earphone on the ear according to the sixth embodiment of the present application. As illustrated in FIG. 6, in this embodiment, like the embodiment illustrated in FIG. 4, during biological feature detection, the light receiving unit 102 is fitted to the inner-side region of the tragus, and the light emitting unit 101 is further located in a connection region between the intertragic notch and the outer ear cannel entrance and is also fitted to a feature region enclosed by the tragus, the antitragus and the intertragic notch. Since the arterial branches and the vein branches are densely distributed in the inner-side region of the tragus 212 and the connection region between the intertragic notch and the outer ear canal entrance, and the flatness is good, the light receiving unit 102 and the light emitting unit 101 may be seamlessly fitted to the ear.

It should be noted that in another embodiment, the light emitting unit 101 is fitted to the intertragic notch, and the light receiving unit 102 is further located in the connection region between the intertragic notch and the outer ear canal entrance and is located in the feature region enclosed by the tragus, the antitragus and the intertragic notch.

In this embodiment, similar to the embodiment illustrated in FIG. 4, to enable the light receiving unit 102 and the light emitting unit 101 to be closely fitted to the inner-side region of the tragus 212 and the connection region between the intertragic notch and the outer ear canal entrance, the light receiving unit 102 and the light emitting unit 101 may be integrated at a shell fitted to the inner-side region of the tragus 212 and at a shell fitted to the connection region between the intertragic notch and the outer ear canal entrance after the earphone is worn, with no need to arrange an assistance mechanism, such that the biological feature detection apparatus including the light receiving unit 102 and the light emitting unit 101 are integrally closely fitted to ear.

Figure 7:
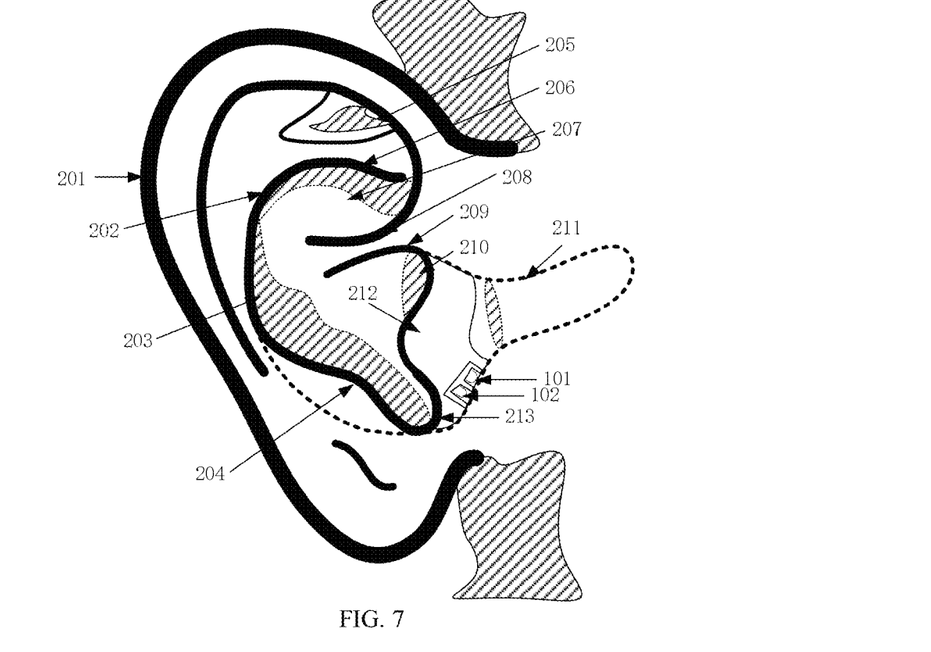
FIG. 7 is a schematic diagram of wearing an earphone on the ear according to the seventh embodiment of the present application.

FIG. 7 is a schematic diagram of wearing an earphone on the ear according to the seventh embodiment of the present application. As illustrated in FIG. 7, in this embodiment, the light emitting unit 101 and the light receiving unit 102 are both located in the connection region between the intertragic notch and the outer ear canal entrance, and are also located in the feature region enclosed by the tragus, the antitragus and the intertragic notch.

In this embodiment, similar to the embodiment illustrated in FIG. 4, to enable the light receiving unit 102 and the light emitting unit 101 to be closely fitted to the connection region between the intertragic notch and the outer ear canal entrance, the light receiving unit 102 and the light emitting unit 101 may be integrated at a shell fitted to the connection region between the intertragic notch and the outer ear canal entrance after the earphone is worn, with no need to arrange an assistance mechanism, such that the biological feature detection apparatus including the light receiving unit 102 and the light emitting unit 101 are integrally closely fitted to the inner-side region of the tragus.

Figure 8:
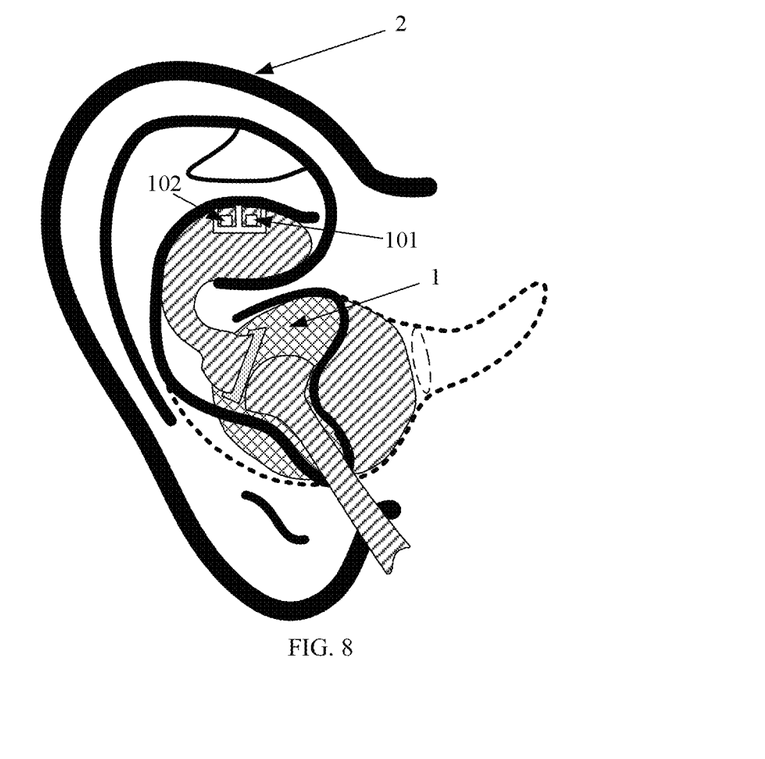
FIG. 8 is a schematic diagram of wearing an earphone on the ear according to the eighth embodiment of the present application.

FIG. 8 is a schematic diagram of wearing an earphone on the ear according to the eighth embodiment of the present application. As illustrated in FIG. 8, the light receiving unit 102 and the light emitting unit 101 are fitted to a region between the inferior crus of antihelix and the crus of helix.

In this embodiment, the earphone may further include: a wearing assistance mechanism 110. The light receiving unit 102 and the light emitting unit 101 are arranged on the wearing assistance mechanism 101, such that the light receiving unit 102 and the light emitting unit 101 are fitted to the region between the inferior crus of antihelix and the crus of helix.

In another embodiment, as illustrated in FIG. 8, the light receiving unit 102 and the light emitting unit 101 are fitted to a region between the antihelix and the crus of helix.

In another embodiment, the wearing assistance mechanism 110 may also be detached from the earphone, such that the wearing assistance mechanism 110 is assembled to the earphone where biological feature detection is desired, and is detached from the earphone where biological feature detection is not desired. In this way, the earphone and the wearing assistance mechanism 110 may flexibly cooperate with each other.

During practice, one end of the wearing assistance mechanism 110 may be fixed to the shell of the earphone, and the other end of the wearing assistance mechanism 110 is provided with the light receiving unit 102 and the light emitting unit 101.

Figure 9:
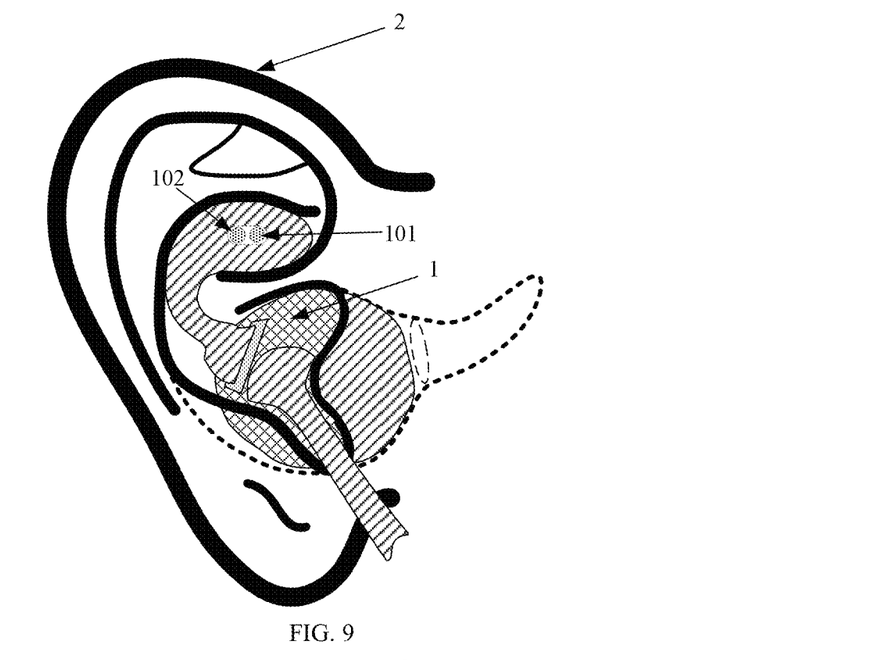
FIG. 9 is a schematic diagram of wearing an earphone on the ear according to the ninth embodiment of the present application.

FIG. 9 is a schematic diagram of wearing an earphone on the ear according to the ninth embodiment of the present application. As illustrated in FIG. 9, in this embodiment, the light receiving unit 102 and the light emitting unit 101 are both fitted to a region of the cimba concha; in another embodiment, either the light receiving unit 102 or the light emitting unit 101 is fitted to the region of the cimba concha.

In the embodiments illustrated in FIG. 4 to FIG. 9, biological feature detection is carried out based on the light reflection theory. However, it should be noted that the position of the light receiving unit 102 or the light emitting unit 101 may be correspondingly adjusted to carry out biological feature detection based on the light projection theory.

In another embodiment, the light receiving unit 102 is fitted to the region of the cimba concha, and the light emitting unit 101 is fitted to a behind-the-ear region corresponding to the region of the cimba concha. Accordingly, biological feature detection may be carried out based on the light projection theory.

Figure 10:
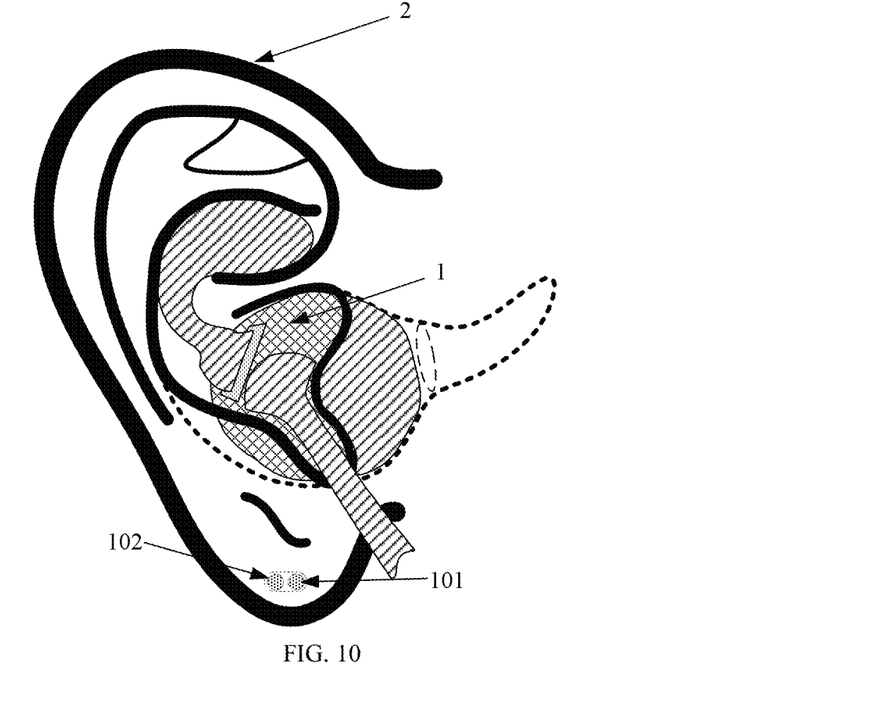
FIG. 10 is a schematic diagram of wearing an earphone on the ear according to the tenth embodiment of the present application.

FIG. 10 is a schematic diagram of wearing an earphone on the ear according to the tenth embodiment of the present application. As illustrated in FIG. 10, the light receiving unit 102 and the light emitting unit 101 are both fitted to a region of the earlobe. In this embodiment, the light receiving unit 102 and the light emitting unit 101 are arranged on the same side of the region of the earlobe. Accordingly, biological feature detection may be carried out based on the light projection theory.

Figure 11:
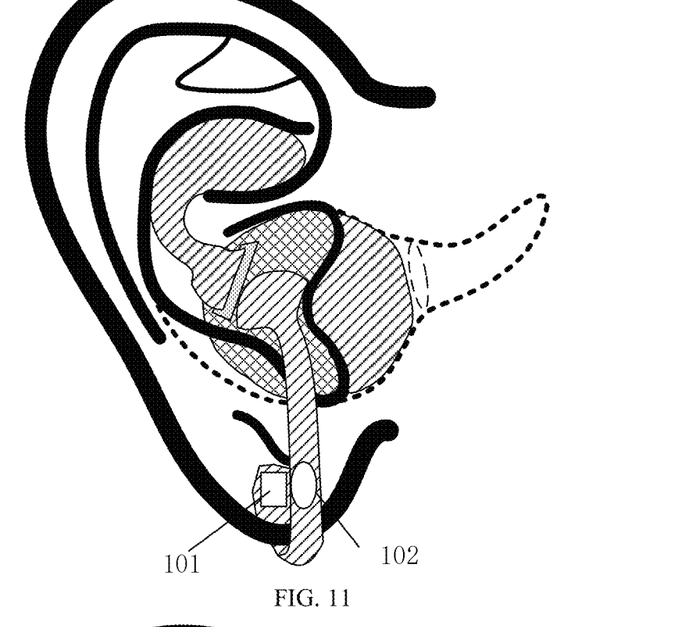
FIG. 11 is a schematic diagram of wearing an earphone on the ear according to the eleventh embodiment of the present application.

In addition, if the light receiving unit 102 and the light emitting unit 101 are respectively arranged on two sides of the region of the earlobe, biological feature detection may be correspondingly carried out based on the light projection theory. Referring to FIG. 11, a schematic diagram of wearing an earphone on the ear according to the eleventh embodiment of the present application is given.

Figure 12:
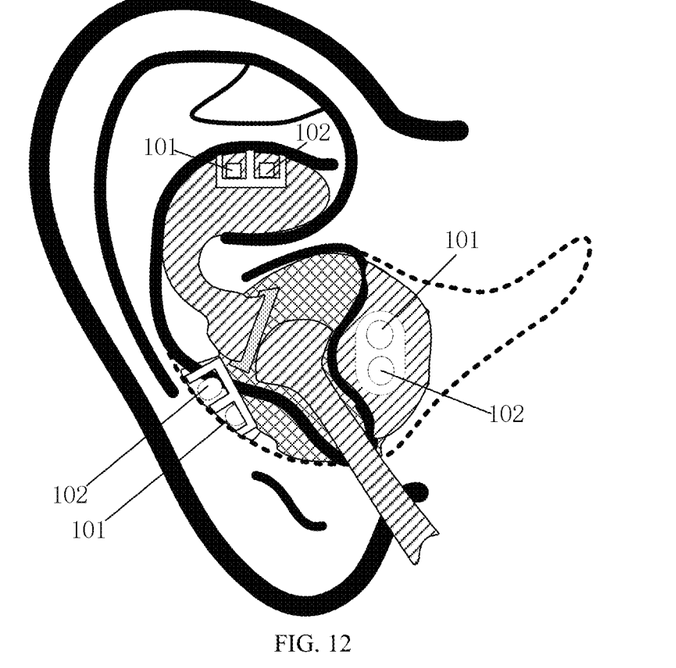
FIG. 12 is a schematic diagram of wearing an earphone on the ear according to the twelfth embodiment of the present application.

FIG. 12 is a schematic diagram of wearing an earphone on the ear according to the twelfth embodiment of the present application. As illustrated in FIG. 12, different from the above embodiment, the earphone is provided with three pairs of light emitting units 101 and light receiving units 102. Specifically, as illustrated in FIG. 12, the three pairs of light emitting unit 101 and light receiving unit 102 are respectively arranged in the inner-side region of the tragus, in the region between the inferior crus of helix and the crus of helix and in the region of the concha cavity.

Figure 13:
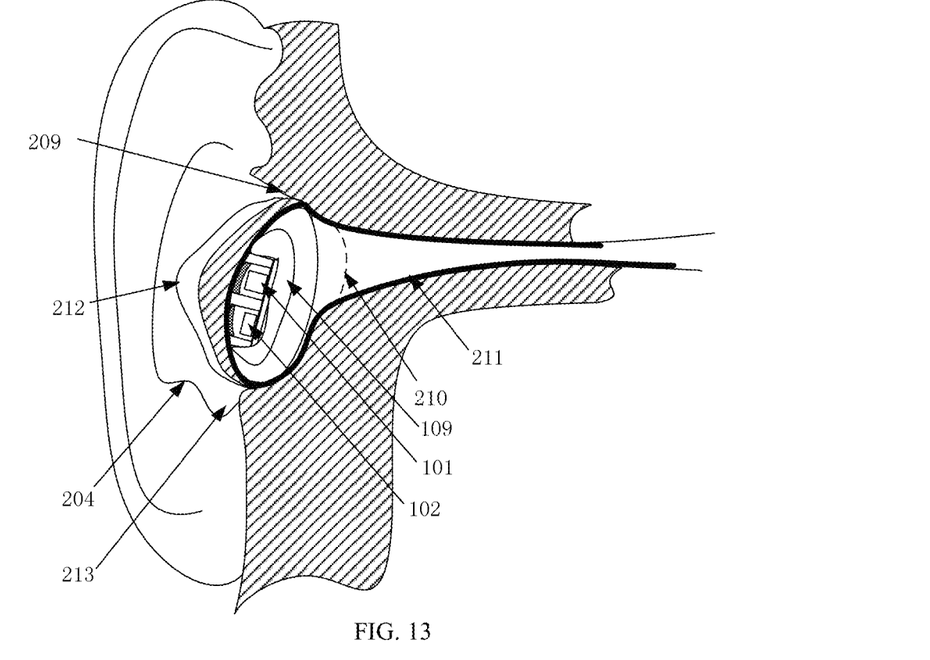
FIG. 13 is a schematic diagram of wearing an earphone on the ear according to the thirteenth embodiment of the present application.

FIG. 13 is a schematic diagram of wearing an earphone on the ear according to the thirteenth embodiment of the present application. As illustrated in FIG. 13, in this embodiment, an elastic unit 109 is additionally arranged. During biological feature detection, the elastic unit 109 enables the light emitting unit 101 and the light receiving unit 102 to be closely fitted to the detection surface of the ear. In this embodiment, using the scenario where an elastic unit is added based on the embodiment illustrated in FIG. 5 as an example, as illustrated in FIG. 13, the elastic unit 109 is arranged in a peripheral region of the ear distal from the outer ear canal entrance, such that the light emitting unit 101 and the light receiving unit 102 are pressed and thus are closely fitted to the detection surface of the ear.

Alternatively, in another embodiment, the elastic unit 109 may only press the light emitting unit 101 and the light receiving unit 102, such that the pressed light emitting unit 101 or the pressed light receiving unit 102 is closely fitted to the detection surface of the ear.

In the embodiment including the elastic unit 109, even in the movement, the light emitting unit 101 and/or the light receiving unit 102 may still be closely fitted to the detection surface of the ear. This may prevent the biological feature detection apparatus from sliding relative to the detection surface, such that stability and strength of the detection signal are improved. In addition, this also mitigates or eliminates adverse impacts caused by the movement to the signal-to-noise ratio of the detection signal, and further improves the signal-to-noise ratio of the original electrical signal.

In the above embodiment, the elastic unit 109 may be made of a soft silicone material. The elastic unit 109 may be specifically arranged inside the shell of the earphone.

Figure 14:
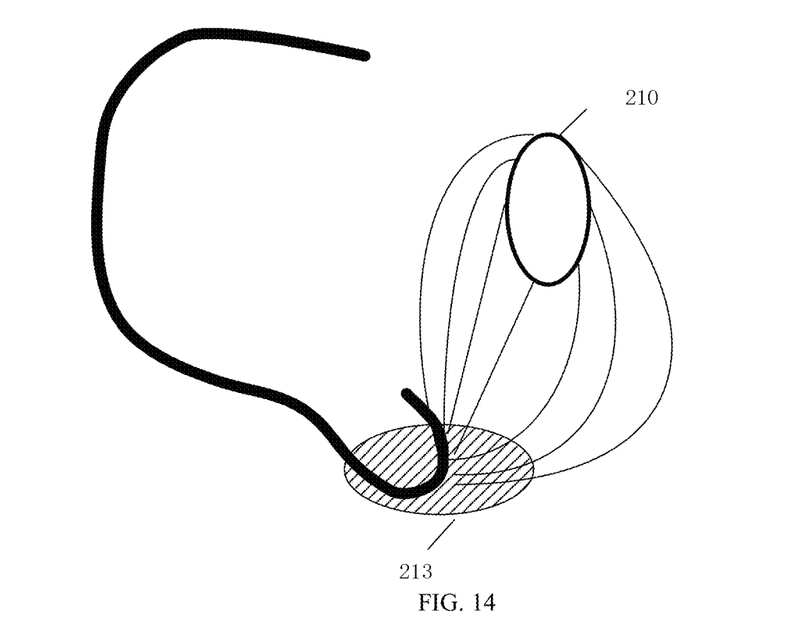
FIG. 14 is a schematic diagram of a connection region between an intertragic notch and an outer ear canal entrance according to the fourteenth embodiment of the present application.

FIG. 14 is a schematic diagram of a connection region between an intertragic notch and an outer ear canal entrance according to the fourteenth embodiment of the present application. As illustrated in FIG. 14, a plurality of connection lines are presented in the connection region between the intertragic notch and the outer ear canal entrance, which is also referred to as formation of a connection cluster. During arrangement of the light emitting unit or the light receiving unit, the light emitting unit or the light receiving unit may be specifically arranged on any connection line in the connection cluster.

Figure 15:
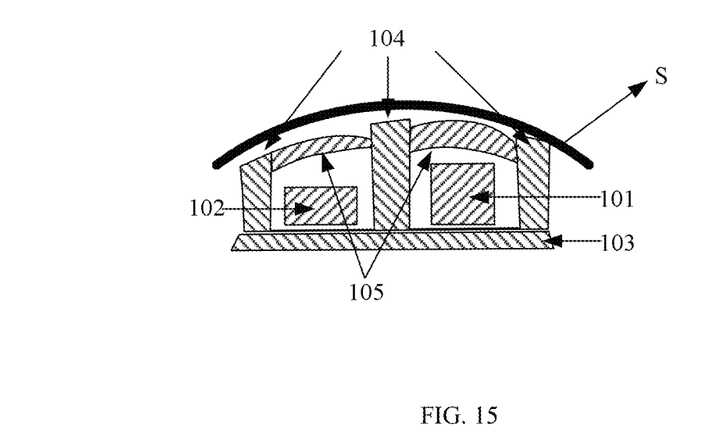
FIG. 15 is a schematic structural diagram of a biological feature detection apparatus according to the fifteenth embodiment of the present application.

FIG. 15 is a schematic structural diagram of a biological feature detection apparatus according to the fifteenth embodiment of the present application. In this embodiment, a biological feature detection apparatus 1 includes a light emitting unit 101 and a light receiving unit 102. The light emitting unit 101 is configured to emit light to a detection surface of a biological tissue (for example, an ear), the light emitted by the light emitting unit 101 is processed by the biological tissue and then transmitted to the light receiving unit 102, and the light receiving unit 102 is configured to receive the light and perform a photoelectric conversion to generate an original electrical signal for biological feature detection. The light emitting unit 101 and the light receiving unit 102 are fitted to the detection surface of the biological tissue to improve a signal-to-noise ratio of the original electrical signal.

Alternatively, in this embodiment, the biological feature detection apparatus may further include a hard substrate 103. The light emitting unit 101 and the light receiving unit 102 are both arranged on the hard substrate 103.

Optionally, in this embodiment, the biological feature detection apparatus may further include: an optical shielding unit 104, configured to shield or absorb the light emitted by the light emitting unit to prevent the light emitted by the light emitting light from being directly transmitted to the light receiving unit without being processed by the biological tissue, and hence to improve accuracy of biological feature detection.

Optionally, in this embodiment, the biological feature detection apparatus may further include: a light guiding unit 105, configured to guide the light emitted by the light emitting unit to the detection surface of the biological tissue, and/or configured to guide the light being processed by the biological tissue to the light receiving unit. Specifically, a light guiding unit 105 may be arranged on each of the light emitting unit 101 and the light receiving unit 102. That is, the biological feature detection apparatus includes two light guiding units 105. The two light guiding units 105 may be integrally arranged or separately arranged. That is, the light guiding unit 105 on the light emitting unit 101 and the light guiding unit 105 on the light receiving unit 102 may be integrally arranged or separately arranged. However, it should be noted that a light guiding unit 105 may also be arranged on either the light emitting unit 101 or the light receiving unit 102. That is, the biological feature detection apparatus includes one light guiding unit 105. In this embodiment, the light guiding unit 105 improves efficiency of light transmission and lowers entire power consumption of the apparatus.

If the optical shielding unit and the light guiding unit are both arranged, the optical shielding unit and the light guiding unit are integrally arranged, or the optical shielding unit and the light guiding unit are separately arrange.

Specifically, when the optical shielding unit 104 and the light guiding unit 105 are both arranged on the biological feature detection apparatus, the optical shielding unit 104 and the light guiding unit 105 are integrally arranged, or the optical shielding unit 104 and the light guiding unit 105 are separately arranged.

During practice, the light guiding unit slightly protrudes from the shell of the earphone to be closely fitted to the detection surface of the ear. In this way, efficiency of light transmission is improved, the signal-to-noise ratio is enhanced, and the entire power consumption of the biological feature detection apparatus is lowered.

In this embodiment, surfaces, facing toward the detection surface, of the light guiding unit 105 and the optical shielding unit 104 are defined to match with the detection surface of the biological tissue. If the detection surface is a planar surface, the surfaces, facing toward the detection surface, of the light guiding unit 105 and the optical shielding unit 104 are also planar surfaces; if the detection surface is an arc surface, the surfaces, facing toward the detection surface, of the light guiding unit 105 and the optical shielding unit 104 are also arc surfaces; and if the detection surface is an irregular surface, the surfaces, facing toward the detection surface, of the light guiding unit 105 and the optical shielding unit 104 are also irregular curved surfaces. It should be noted that the surface, facing toward the detection surface, of the light guiding unit 105 or the optical shielding unit 104 may be defined to match with the detection surface of the biological tissue according to the structure design needs.

In this embodiment, when the light guiding unit is included, the light guiding unit also acts as a cover. Therefore, the surface, facing toward the detection surface, of the light guiding unit is approximately an arc surface, such that the light guiding unit is seamlessly fitted to the inner-side region of the tragus, and thus efficiency of light transmission is improved. During practice, the light guiding unit may slightly protrude from the shell of the earphone to be closely fitted to the inner-side region of the tragus.

In another embodiment, based on the embodiment illustrated in FIG. 15, the biological feature detection apparatus may further include a processing circuit. The processing circuit is configured to perform an analog-to-digital conversion for the original electrical signal to form a digital signal and filters the digital signal; and/or further comprising: a control circuit, wherein the control circuit is configured to control the light emitting unit to emit light to the biological tissue and control the light receiving unit to receive the light.

It should be noted that functionality of the processing circuit may be extended according to the actual needs, which is not limited to analog-to-digital conversion and filter processing.

In another embodiment, based on the embodiment illustrated in FIG. 15, the biological feature detection apparatus may further include a processor. The processor is configured to perform biological feature detection according to the original electrical signal. During biological feature detection performed by the processor according to the original electrical signal, a biological feature signal may be specifically extracted from a digital signal experiencing analog-to-digital conversion and filter processing by the processing circuit; or the processor directly performs analog-to-digital conversion and filtering for the original electrical signal, and then performs biological feature detection. It should be noted that the processor may be an independently configured microprocessor, or may be the processor of the terminal connected to the earphone.

Figure 16:
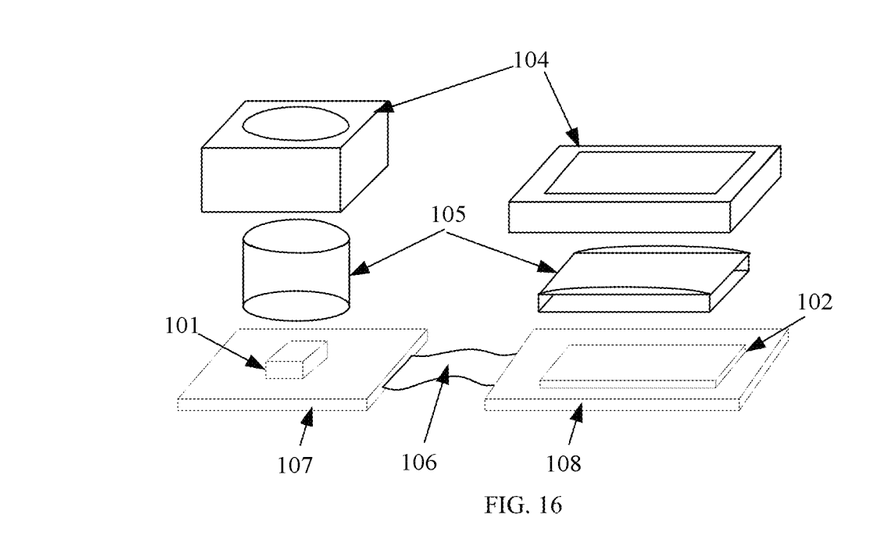
FIG. 16 is a schematic structural diagram of a biological feature detection apparatus according to the sixteenth embodiment of the present application.

FIG. 16 is a schematic structural diagram of a biological feature detection apparatus according to the sixteenth embodiment of the present application. As illustrated in FIG. 16, in this embodiment, using an exploded schematic diagram as an example, like the embodiment illustrated in FIG. 15, the biological feature detection apparatus likewise includes: a light emitting unit 101 and a light receiving unit 102. Different from the above embodiment, the biological feature detection apparatus further includes: a flexible member and two substrates. The two substrates are respectively a first substrate 107 and a second substrate 108. The light emitting unit 101 is arranged on the first substrate 107, and the light receiving unit 102 is arranged on the second substrate 108. In this embodiment, the first substrate 107 and the second substrate 108 are both rigid substrates.

It should be noted that, alternatively, the light emitting unit 101 and the light receiving unit 102 may also be arranged on the same rigid substrate or flexible substrate.

In this embodiment, the light emitting unit 101 is approximately a columnar light source, and the light receiving unit 102 is approximately a planar array to receive the light with a greater light sensing area as much as possible.

In this embodiment, the light emitting unit 101 and the light receiving unit 102 are connected to each other via the flexible member 106. The flexible member is configured to adjust a relative position and/or a relative angle between the light emitting unit 101 and the light receiving unit 102.

Optionally, in this embodiment, the relative position is a linear distance between a geometric center of the light emitting unit 101 and a geometric center of the light receiving unit 102, and/or the relative angle is a normal angle between an outer surface of the light emitting unit 1014 and an outer surface of the light receiving unit 102.

Optionally, in any embodiment of the present application, a normal of the light receiving unit 102 facing towards an outer surface of the detection surface is parallel to a normal of the detection surface; and/or a normal of the light emitting unit 101 facing towards an outer surface of the detection surface is parallel to a normal of the detection surface.

It should be noted that, alternatively, in another embodiment, either the first substrate or the second substrate is a rigid substrate; or alternatively, either the first substrate or the second substrate is a flexible substrate, or both the first substrate and the second substrate are flexible substrates. Further, the flexible member may be a partial structure of the flexible substrate.

In another embodiment, the light emitting unit 101 and the light receiving unit 102 may be separately arranged from the processing circuit in terms of physical aspect, or may be integrally arranged with the processing circuit.

In another embodiment, the light emitting unit 101, the light receiving unit 102, the processing circuit and the processor are physically separated structures, or may be integrated to form a chip structure.

In another embodiment, the biological feature detection apparatus may include a plurality of light emitting units and one light receiving unit, to improve emission efficiency of incident light.

In another embodiment, the biological feature detection apparatus may include a plurality of light receiving units and one light emitting unit, to improve reception efficiency of light.

In the above embodiment including the flexible member, due to presence of the flexible member, the relative position and the relative angle between the light emitting unit and the light receiving unit may be adjusted as needed, such that the biological feature detection apparatus is suitable for the detection surface having any shape.

In addition, when the embodiment illustrated in FIG. 2 is applied to the specific product of the earphone, by adjustments of the relative position and the relative angle between the light emitting unit and the light receiving unit enable the entire earphone product to have a relatively compact structure.

An embodiment of the present application further provides an electronic terminal. The electronic terminal includes the above biological feature detection apparatus. The electronic terminal includes, but not limited to, a smart earphone, a smart bracelet, a smart watch, a smart cap, smart shoes, or smart clothing or the like wearable smart device practiced in any form.

The above described device embodiments are merely for illustration purpose only. The modules which are described as separate components may be physically separated or may be not physically separated, and the components which are illustrated as modules may be or may not be physical modules, that is, the components may be located in the same position or may be distributed into a plurality of network modules. Apart or all of the modules may be selected closely the actual needs to achieve the objectives of the technical solutions of the embodiments. Persons of ordinary skill in the art may understand and implement the present application without paying any creative effort.

Although the preferred embodiments of the present application are described above, once knowing the basic creative concept, a person skilled in the art can make other modifications and variations to these embodiments. Therefore, the appended claims are intended to be construed as covering the preferred embodiments and all the modifications and variations falling within the scope of the present application. Obviously, a person skilled in the art can make various modifications and variations to the present application without departing from the spirit and scope of the present application. In this way, the present application is intended to cover the modifications and variations if they fall within the scope of the appended claims of the present application and equivalent technologies thereof.

What is claimed is:

1. A biological feature detection apparatus, comprising a light emitting unit and a light receiving unit; wherein the light emitting unit is configured to emit light to a detection surface of a biological tissue, the light emitted by the light emitting unit is reflected by the biological tissue and then transmitted to the light receiving unit, and the light receiving unit is configured to receive the light and perform a photoelectric conversion to generate an original electrical signal for biological feature detection; the light emitting unit and the light receiving unit are configured to be fitted the detection surface of the biological tissue to improve a signal-to-noise ratio of the original electrical signal; the biological tissue is an ear, and during biological feature detection, at least one of the light receiving unit and the light emitting unit is configured to be fitted to a tragus inner-side region; or at least one of the light receiving unit and the light emitting unit is configured to be fitted to a region between an inferior crus of antihelix and a crus of helix; or at least one of the light receiving unit and the light emitting unit is configured to be fitted to a region between an antihelix and a crus of helix; or at least one of the light receiving unit and the light emitting unit is configured to be fitted to a cimba concha region; or at least one of the light receiving unit and the light emitting unit is configured to be fitted to an earlobe region; or at least one of the light receiving unit and the light emitting unit is located in a concha cavity; or at least one of the light receiving unit and the light emitting unit is located in a region enclosed by the crus of helix, an ear canal entrance and the antihelix close to an antitragus, wherein the biological feature detection apparatus further comprises a first rigid substrate, a second rigid substrate, and a flexible member; the light emitting unit is arranged on the first rigid substrate, the light receiving unit is arranged on the second rigid substrate, the first rigid substrate and the second rigid substrate are connected via the flexible member, at least one of a relative position and a relative angle between the light emitting unit and the light receiving unit is adjustable via the flexible member, and the light emitting unit and the light receiving unit are integrated at a shell of the biological feature detection apparatus.

2. The detection apparatus according to claim 1, wherein: when the light receiving unit is configured to be fitted to the tragus inner-side region, the light emitting unit is located in an underneath connection region between an intertragic notch and an outer ear canal entrance; or when the light emitting unit is configured to be fitted to the tragus inner-side region, the light receiving unit is located in an underneath connection region between an intertragic notch and an outer ear canal entrance.

3. The detection apparatus according to claim 1, further comprising: a wearing assistance mechanism; wherein the light receiving unit and the light emitting unit are arranged on the wearing assistance mechanism, such that at least one of the light receiving unit and the light emitting unit is configured to be fitted to the region between the inferior crus of antihelix and the crus of helix or such that at least one of the light receiving unit and the light emitting unit is configured to be fitted to the region between the antihelix and the crus of helix.

4. The detection apparatus according to claim 1, further comprising: a wearing assistance mechanism; wherein the light receiving unit and the light emitting unit are arranged on the wearing assistance mechanism, such that at least one of the light receiving unit and the light emitting unit is configured to be fitted to the region between the inferior crus of antihelix and the crus of helix or such that at least one of the light receiving unit and the light emitting unit is configured to be fitted to the region between the antihelix and the crus of helix.

5. The detection apparatus according to claim 1, further comprising:
an optical shielding unit, configured to shield or absorb the light emitted by the light emitting unit to prevent the light emitted by the light emitting light from being directly transmitted to the light receiving unit without being reflected by the biological tissue; and/or
a light guiding unit, configured to guide the light emitted by the light emitting unit to the detection surface of the biological tissue, and/or configured to guide the light being reflected by the biological tissue to the light receiving unit.

6. The detection apparatus according to claim 5, wherein the optical shielding unit and the light guiding unit are integrally arranged, or the optical shielding unit and the light guiding unit are separately arranged.

7. The detection apparatus according to claim 6, wherein a surface of the light guiding unit and/or the optical shielding unit is shaped to match the detection surface of the biological tissue.

8. The detection apparatus according to claim 1, further comprising:
a processing circuit, wherein the processing circuit is configured to perform an analog-to-digital conversion for the original electrical signal to form a digital signal and filters the digital signal; and/or
a control circuit, wherein the control circuit is configured to control the light emitting unit to emit light to the biological tissue and control the light receiving unit to receive the light.

9. The detection apparatus according to claim 1, further comprising: a processor; wherein the processor is configured to perform biological feature detection based on the original electrical signal.

10. The detection apparatus according to claim 1, wherein the relative position is a linear distance between a geometric center of the light emitting unit and a geometric center of the light receiving unit, and the relative angle is a normal angle between an outer surface of the light emitting unit and an outer surface of the light receiving unit.

11. The detection apparatus according to claim 1, wherein a normal of the light receiving unit facing towards an outer surface of the detection surface is parallel to a normal of a detection surface of the light receiving unit; or a normal of the light emitting unit facing towards an outer surface of the detection surface is parallel to a normal of the detection surface.

12. The detection apparatus according to claim 1, wherein the biological feature is a heart rate feature and a blood oxygen feature based on a photoplethysmogram signal.

13. The detection apparatus according to claim 1, further comprising: an elastic unit; wherein, during biological feature detection, the elastic unit is configured to enable the light emitting and/or the light receiving unit to be closely fitted to the detection surface of the biological tissue.

14. An electronic terminal, comprising a biological feature detection apparatus, wherein the biological feature detection apparatus comprises a light emitting unit and a light receiving unit; wherein the light emitting unit is configured to emit light to a detection surface of a biological tissue, the light emitted by the light emitting unit is reflected by the biological tissue and then transmitted to the light receiving unit, and the light receiving unit is configured to receive the light and perform a photoelectric conversion to generate an original electrical signal for biological feature detection; the light emitting unit and the light receiving unit are configured to fit the detection surface of the biological tissue to improve a signal-to-noise ratio of the original electrical signal; the biological tissue is an ear, and during biological feature detection, at least one of the light receiving unit and the light emitting unit is configured to be fitted to a tragus inner-side region; or at least one of the light receiving unit and the light emitting unit is fitted to a region between an inferior crus of antihelix and a crus of helix; or at least one of the light receiving unit and the light emitting unit is configured to be fitted to a region between an antihelix and a crus of helix; or at least one of the light receiving unit and the light emitting unit is configured to be fitted to a cimba concha region; or at least one of the light receiving unit and the light emitting unit is configured to be fitted to an earlobe region; or at least one of the light receiving unit and the light emitting unit is located in a concha cavity; or at least one of the light receiving unit and the light emitting unit is located in a region enclosed by the crus of helix, an ear canal entrance and the antihelix close to an antitragus, wherein the biological feature detection apparatus further comprising a first rigid substrate, a second rigid substrate, and a flexible member; the light emitting unit is arranged on the first rigid substrate, the light receiving unit is arranged on the second rigid substrate, the first rigid substrate and the second rigid substrate are connected via the flexible member, at least one of a relative position and a relative angle between the light emitting unit and the light receiving unit is adjustable via the flexible member, and the light emitting unit and the light receiving unit are integrated at a shell of the biological feature detection apparatus.

* * * * *